United States Patent [19]

Adams et al.

[11] Patent Number: 5,265,600

[45] Date of Patent: Nov. 30, 1993

[54] ATRIAL DEFIBRILLATOR AND METHOD FOR PROVIDING POST-CARDIOVERSION PACING

[75] Inventors: John M. Adams, Issaquah; Kenneth R. Infinger, Redmond, both of Wash.

[73] Assignee: InControl, Inc., Redmond, Wash.

[21] Appl. No.: 965,156

[22] Filed: Oct. 23, 1992

[51] Int. Cl.⁵ .................... A61N 1/39; A61N 1/362
[52] U.S. Cl. ........................................................ 607/4
[58] Field of Search ..................... 128/419 D, 419 PG

[56] References Cited

U.S. PATENT DOCUMENTS

| | | | |
|---|---|---|---|
| 3,738,370 | 6/1973 | Charms | 128/419 D |
| 3,952,750 | 4/1976 | Mirowski et al. | 128/419 D |
| 4,163,451 | 8/1979 | Lesnick et al. | 128/419 PG |
| 4,384,585 | 5/1983 | Zipes | 128/419 D |
| 4,407,288 | 10/1983 | Langer et al. | 128/419 D |
| 4,895,151 | 1/1990 | Grevis et al. | 128/419 D |
| 4,932,407 | 6/1990 | Williams | 128/419 D |
| 5,002,052 | 3/1991 | Haluska | 128/419 PG |
| 5,014,696 | 5/1991 | Mehra | 128/419 D |
| 5,074,301 | 12/1991 | Gill | 128/419 D |
| 5,078,133 | 1/1992 | Heinz et al. | 128/419 PG |
| 5,086,772 | 2/1992 | Larnard et al. | 128/419 D |
| 5,129,394 | 7/1992 | Mehra | 128/419 D |
| 5,161,527 | 11/1992 | Nappholz et al. | 128/419 D |
| 5,165,403 | 11/1992 | Mehra | 128/419 D |

*Primary Examiner*—William E. Kamm
*Assistant Examiner*—Kennedy J. Schaetzle
*Attorney, Agent, or Firm*—Foley & Lardner

[57] ABSTRACT

An implantable atrial defibrillator applies cardioverting electrical energy to the atria of a human heart in need of cardioversion and thereafter gradually returns the cardiac rate of the heart to a normal cardiac rate. The atrial defibrillator includes a first detector for detecting atrial activity of the heart, and an atrial fibrillation detector, responsive to said first detector, for determining when the atria of the heart are in need of cardioversion. The atrial defibrillator further includes a cardioverter responsive to the atrial fibrillation detector for applying the cardioverting electrical energy to the atria of the heart when the atria are in need of cardioversion, and a pacing output for pacing the ventricles of the heart at a decreasing cardiac rate from a base rate to a final rate lower than the base rate after the atria of the heart are successfully cardioverted.

22 Claims, 2 Drawing Sheets

ATRIAL DEFIBRILLATOR AND METHOD FOR PROVIDING POST-CARDIOVERSION PACING

BACKGROUND OF THE INVENTION

The present invention generally relates to an atrial defibrillator and method for applying cardioverting electrical energy to the atria of a human heart in need of cardioversion. The present invention is more particularly directed to a fully automatic implantable atrial defibrillator which exhibits improved safety by reducing the potential risk of induced ventricular fibrillation which may result from the delivery of cardioverting electrical energy to the atria. More specifically, the atrial defibrillator and method of the present invention returns the heart gradually to a normal cardiac rate by pacing the ventricles at gradually decreasing cardiac rates until a preselected normal cardiac rate is obtained after applying cardioverting electrical energy to the atria.

Atrial fibrillation is probably the most common cardiac arrythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient b way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistent to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Implantable atrial defibrillators proposed in the past have exhibited a number of disadvantages which probably has precluded these defibrillators from becoming a commercial reality. Two such proposed defibrillators, although represented as being implantable, were not fully automatic, requiring human interaction for cardioverting or defibrillating the heart. Both of these proposed defibrillators require the patient to recognize the symptoms of atrial fibrillation with one defibrillator requiring a visit to a physician to activate the defibrillator and the other defibrillator requiring the patient to activate the defibrillator with an external magnet.

Improved atrial defibrillators and lead systems which exhibit both automatic operation and improved safety are fully described in copending U.S. application Ser. No. 07/685,130, filed Apr. 12, 1991, in the names of John M. Adams and Clifton A. Alferness for IMPROVED ATRIAL DEFIBRILLATOR AND METHOD and U.S. application Ser. No. 07/856,514, filed Mar. 24, 1992, in the names of John M. Adams, Clifton A. Alferness, and Paul E. Kreyenhagen for IMPROVED ATRIAL DEFIBRILLATOR, LEAD SYSTEMS, AND METHOD, which applications are assigned to the assignee of the present invention an incorporated herein by reference. As disclosed in the aforementioned referenced applications, synchronizing the delivery of the defibrillating or cardioverting electrical energy to the atria with a ventricular electrical activation (R wave) of the heart has been considered important to avoid cardioverting the heart during the heart's vulnerable period or T wave to thus prevent induced ventricular fibrillation. Ventricular fibrillation is a fatal arrythmia which can be caused by electrical energy being delivered to the heart at the wrong time in the cardiac cycle, such as during the T wave of the cycle. The atrial defibrillators of the aforementioned referenced applications exhibit improved safety from inducing ventricular fibrillation by sensing ventricular activations of the heart in a manner which avoids detecting noise as ventricular electrical activations for generating reliable synchronization signals. Hence, these implantable atrial defibrillators, by providing such noise immunity in R wave detection assure reliable synchronization.

Another measure for reducing the risk of inducing ventricular fibrillation during the delivery of cardioverting electrical energy to the atria of the heart employed by the defibrillators of the aforementioned referenced applications is the reduction of the amount of the electrical energy which is passed through the ventricles during cardioversion of the atria. This is achieved by locating the cardioverting electrodes in or near the heart to provide a cardioverting energy path which confines most of the cardioverting electrical energy to the atria of the heart.

It has also been observed that during episodes of atrial fibrillation, the cardiac rate often increases to a high rate and/or becomes extremely variable. At high cardiac rates, the R wave of each cardiac cycle becomes closely spaced to the T wave of the previous cardiac cycle. This may create a condition known in the art as an "R on T" condition which is believed to contribute to induced ventricular fibrillation if the atria are cardioverted in synchronism with an R wave close to the preceding T wave. For highly variable cardiac rates, a long cardiac cycle can be followed by a relatively short cardiac cycle. This condition is believed to cause a dispersion of refractoriness and also can result in a vulnerable R on T condition.

To avoid applying the cardioverting electrical energy to the atria during a vulnerable R on T condition, an atrial defibrillator fully described in copending application U.S. Ser. No. 07/965,168, filed concurrently herewith in the names of John M. Adams, Clifton A. Alferness, Kenneth Ross Infinger and Yixuan Jin and entitled ATRIAL DEFIBRILLATOR AND METHOD FOR PROVIDING SYNCHRONIZED DELAYED CARDIOVERSION, which application in incorporated herein by reference, delays the delivery of the cardioverting electrical energy to the atria until after an R wave is detected. This assures that the cardioverting electrical energy is not applied in synchronism with an R wave which is closely adjacent to the T wave of an immediately preceding cardiac cycle.

It has also been observed that after successful cardioversion of the atria, the cardiac rate of the heart will suddenly shift from the aforementioned high rate to a normal sinus rate or even still a lower rate if there is temporary sinoatrial node or atrioventricular node dysfunction resulting from the cardioversion of the atria. Since at high cardiac rates the heart provides low cardiac output due to lowered pumping efficiency, the sudden reduction in cardiac rate could potentially result in the patient experiencing a spell of dizziness. In addition, the sudden reduction in cardiac rate can also lead to dispersion of refractoriness which, if it occurs together with an R on T condition, can render the heart more vulnerable to induced ventricular fibrillation. Hence, such a sudden reduction in cardiac rate following successful cardioversion of the atria may be undesirable.

The atrial defibrillator and method of the present invention overcomes the aforementioned problems connected with the sudden reduction in cardiac rate following successful cardioversion or defibrillation of the atria by gradually returning the cardiac rate to a preselected normal rate after the cardioverting electrical energy is applied to the atria. As will be seen hereinafter, this is accomplished by pacing the ventricles of the heart at gradually decreasing cardiac rate from a base rate determined prior to cardioversion to a final normal rate lower than the base rate after the cardioverting or defibrillating electrical energy is applied to the atria of the heart. Furthermore, pacing of the ventricles is preferably performed in the demand mode, known in the art as the VVI mode, to permit the heart to gradually return to the normal cardiac rate on its own if it is able to do so.

SUMMARY OF THE INVENTION

The present invention therefore provides an implantable atrial defibrillator for providing cardioverting electrical energy to the atria of a human heart in need of cardioversion. The atrial defibrillator includes first detecting means for detecting atrial activity of the heart and atrial fibrillation detecting means responsive to the first detecting means for determining when the atria of the heart are in need of cardioversion. The atrial defibrillator further includes cardioverting means for applying the cardioverting electrical energy to the atria of the heart when the atria of the heart are in need of cardioversion and pacing means for pacing the ventricles of the heart after the cardioverting means applies the cardioverting electrical energy to the atria of the heart.

The present invention further provides a method of applying cardioverting electrical energy to the atria of a human heart in need of cardioversion. The method includes the steps of detecting atrial activity of the heart and determining when the atria of the heart are in need of cardioversion. The method further includes the steps of applying the cardioverting electrical energy to the atria of the heart when the atria of the heart are in need of cardioversion, and pacing the ventricles of the heart after applying the cardioverting electrical energy to the atria of the heart.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
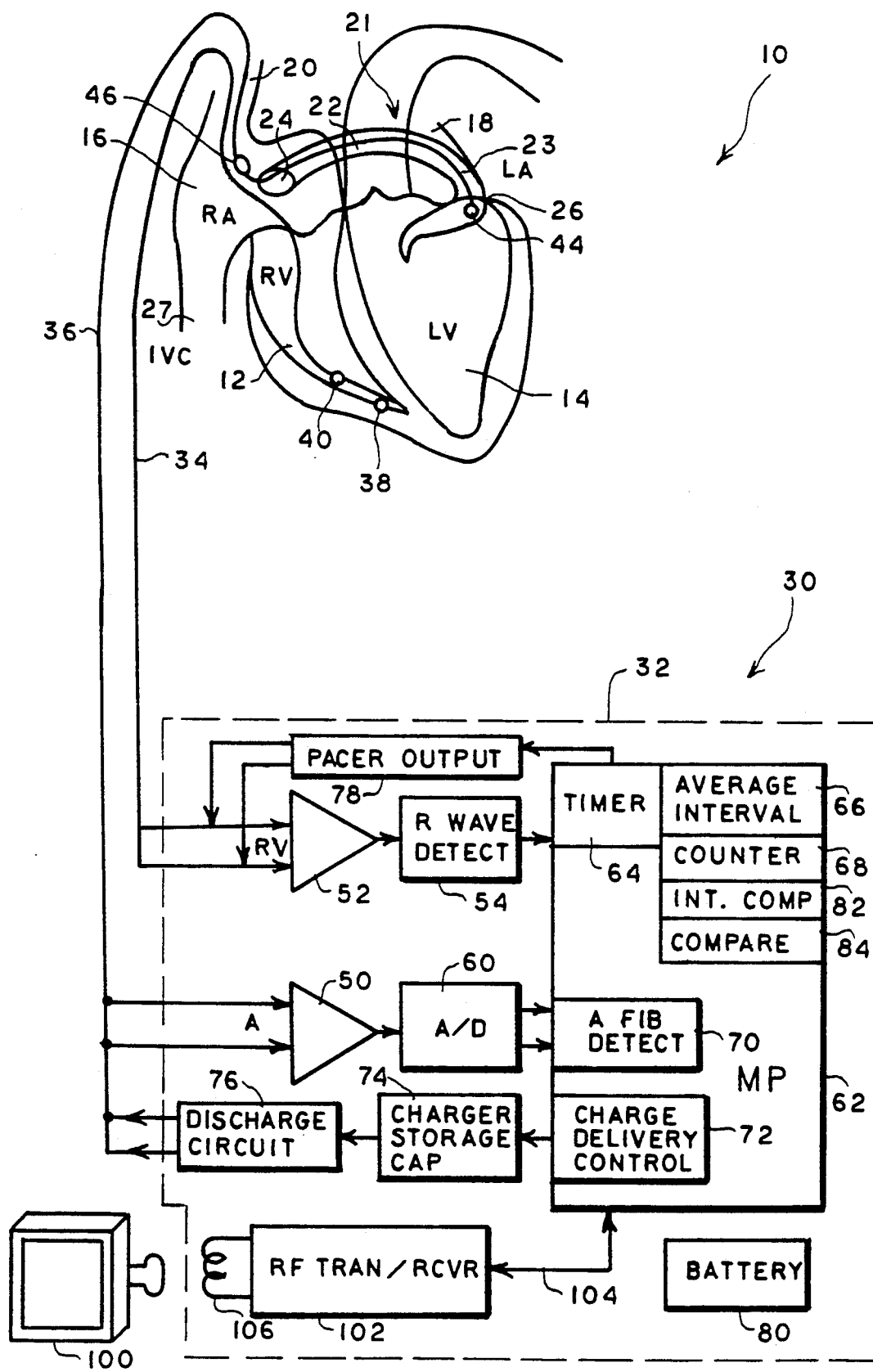
FIG. 1 is a schematic block diagram of a fully implantable atrial defibrillator embodying the present invention for applying defibrillating electrical energy to the atria of a human heart and which is shown in association with a human heart in need of atrial fibrillation monitoring and potential cardioversion of the atria.

Prior to referring to FIG. 1, a general description of a typical electrocardiogram (ECG) cycle may be helpful in understanding the operation and various aspects of the present invention. The ECG cycle begins with a P wave which is normally a small positive wave. The P wave is the depolarization of the atria of the heart. Following the P wave there is an ECG portion which is substantially constant in amplitude. This substantially constant portion will have a time duration on the order of, for example, 120 milliseconds.

The QRS complex of the ECG then normally occurs after the substantially constant portion. The dominating feature of the QRS complex is the R wave which is a rapid positive or negative deflection. The R wave generally has an amplitude greater than any other wave of the ECG and will have a spiked shape of relatively short duration with a sharp rise, a peak amplitude, and a sharp decline. The R wave is the depolarization of the ventricles and hence, as used herein, the term "ventricle activations" denotes R waves of the heart cardiac cycles.

Following the QRS complex, the ECG is completed with the T wave which is separated from the QRS complex by about 250 milliseconds. The T wave is relatively long in duration of, for example, on the order of 150 milliseconds. It is during the T wave that the heart is most vulnerable to induced ventricular fibrillation should the heart be cardioverted during this period. The next ECG cycle begins with the next P wave. The duration of a cardiac cycle may be on the order of 800 milliseconds corresponding to a normal cardiac rate of seventy-five beats per minute.

As will be appreciated by those skilled in the art, the ECG characteristics of a heart experiencing atrial fibrillation will be distinctly different than described above for a heart in normal sinus rhythm. During atrial fibrillation, there generally are no discernable P waves because the atria are in an unstable or fibrillating condition. Also, the cardiac rate is generally elevated to a high rate, such as, for example, 150 beats per minute. As used herein, the term "cardiac cycle" denotes the period of heart activity which begins with each ventricular depolarization and "cardiac rate" denotes the rate of ventricular depolarizations of the heart resulting from either a natural ventricular activation or a ventricular stimulus by pacing the ventricles of the heart.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus channel 21, which, as used herein, denotes the coronary sinus 22 and the great cardiac vein 23, the coronary sinus ostium or opening 24, the left ventricular free wall 26 and the inferior vena cava 27.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises an endocardial bi-polar lead having electrodes 38 and 40 arranged for establishing electrical contact with the right ventricle 12 of the heart 10. The electrodes 38 and 40 permit bi-polar sensing of ventricular activations in the right ventricle. The electrodes 38 and 40 further provide for pacing the ventricles 12 and 14 in a manner to be described hereinafter in accordance with the present invention. As illustrated, the lead 34 is fed through the superior vena cava 20, into the right atrium 16, and then into the right ventricle 12.

The second lead 36 generally includes a first or tip electrode 44 and a second or proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18. The first electrode 44 and the second electrode 46 further provide for the delivery of defibrillating electrical energy to the atria. Because the first electrode 44 is located beneath the left atrium 18 near the left ventricle 14 and the second electrode 46 is within the right atrium 16, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized. This greatly reduces the potential for ventricular fibrillation of the heart to be induced as a result of the application of defibrillating electrical energy of the atria of the heart.

Within the enclosure 32, the atrial defibrillator 30 includes a first sense amplifier 50, a second sense amplifier 52, and an R wave detector 54. The first sense amplifier 50 forms a first detecting means which, together with the lead 36 to which sense amplifier 50 is coupled, senses atrial activity of the heart. The second sense amplifier 52 and the R wave detector 54 form a second detecting means which, together with the lead 34 to which sense amplifier 52 is coupled, detects ventricular activations of the right ventricle of the heart.

The output of the second sense amplifier 52 is coupled to the R wave detector 54. The R wave detector 54 is of the type well known in the art which provides an output pulse upon the occurrence of an R wave being sensed during a cardiac cycle of the heart.

The output of the first sense amplifier 50 is coupled to an analog to digital converter 60. The analog to digital converter 60 converts the analog signal representative of the atrial activity of the heart being detected to digital samples for further processing in a manner to be described hereinafter.

The enclosure 32 of the atrial defibrillator 30 further includes a microprocessor 62. The microprocessor 62 is preferably implemented in a manner as disclosed in the aforementioned copending U.S. application Ser. Nos. 07/685,130 and 07/856,514 and further as described hereinafter with respect to the flow diagram of FIG. 2. The implementation of the microprocessor 62 in accordance with this embodiment of the present invention results in a plurality of functional stages. The stages include a timer 64, an average interval stage 66, a counter stage 68, an atrial arrythmia detector in the form of an atrial fibrillation detector 70, a charge delivery and energy control stage 72, an interval computing stage 82, and an interval compare stage 84.

The microprocessor 62 is arranged to operate in conjunction with a memory (not shown) which may be coupled to the microprocessor 62 by a multiple-bit address bus (not shown) and a bi-directional multiple-bit databus (not shown). This permits the microprocessor 62 to address desired memory locations within the memory for executing write or read operations. During a write operation, the microprocessor stores data, such as time intervals or operating parameters in the memory at the addresses defined by multiple-bit addresses conveyed over the address bus and conveys the data to the memory over the multiple-bit data bus. During a read operation, the microprocessor 62 obtains data from the memory at the storage locations identified by the multiple-bit addresses provided over the address bus and receives the data from the memory over the bi-directional data bus.

For entering operating parameters into the microprocessor 62, such as a preselected final cardiac rate referred to hereinafter, the microprocessor 62 receives such programmable operating parameters from an external controller 100 which is external to the skin of the patient. The external controller 100 is arranged to communicate with a receiver/transmitter 102 which is coupled to the microprocessor 62 over a bi-directional bus 104. The receiver/transmitter 102 may be of the type well known in the art for conveying various information which it obtains from the microprocessor 62 to the external controller 100 or for receiving programming parameters from the external controller 100 which the receiver/transmitter 102 then conveys to the microprocessor 62 for storage in internal memory or in the aforementioned external memory within enclosure 32.

The receiver/transmitter 102 includes a transmitting coil 106 so that the receiver/transmitter 102 and coil 106 form a communication means. Such communication means are well known in the art and may be utilized as noted above for receiving commands from external to the implantable enclosure 3 and for transmitting data to the external controller 100 from the implanted enclosure 32. One such communication system is disclosed, for example, in U.S. Pat. No. 4,586,508.

To complete the identification of the various structural elements within the enclosure 32, the atrial defibrillator 30 further includes a charger and storage capacitor circuit 74 of the type well known in the art which charges a storage capacitor to a predetermined voltage level, a discharge circuit 76 for discharging the storage capacitor within circuit 74 by a predetermined amount to provide a controlled discharge output of electrical energy, when required, to the atria of the heart, and a pacer output circuit 78 for applying pacing electrical energy to the ventricles of the heart.

The discharge circuit 76 is coupled to the first electrode 44 and the second electrode 46 of the second lead 36. This permits the application of the cardioverting or defibrillating electrical energy to the atria.

The pacer output circuit 78 may be of the type well known in the art for providing pacing electrical energy. The pacer output circuit 78 is coupled to electrodes 38 and 40 of lead 34 for applying the pacing electrical energy to the right ventricle 12.

Lastly, the defibrillator 30 includes a depletable power source 80, such a lithium battery. The battery 80 provides power to the electrical components of the atrial defibrillator 30.

The sense amplifier 52 and the R wave detector 54 continuously detect the occurrence of ventricular activations of the right ventricle 12. As disclosed in the aforementioned copending U.S. application Ser. Nos. 07/685,130 and 07/856,514, incorporated herein by reference, when the time intervals between immediately successive R waves indicate the probability of an episode of atrial fibrillation, the microprocessor 62 enables the atrial fibrillation detector 70, sense amplifier 50, and the analog to digital converter 60.

The atrial fibrillation detector 70 then determines, responsive to the detected atrial activity, if the heart is experiencing an episode of atrial fibrillation. For detecting atrial fibrillation, the atrial fibrillation detector may be implemented by any one of the algorithms identified in the aforementioned cross-referenced copending applications incorporated herein by reference. If the atrial fibrillation detector 70 does not detect an episode of atrial fibrillation, it will continue to do so. When the atrial fibrillation detector 70 determines that the heart is experiencing an episode of atrial fibrillation, the microprocessor then proceeds to the operation illustrated in the flow diagram of FIG. 2.

Figure 2:
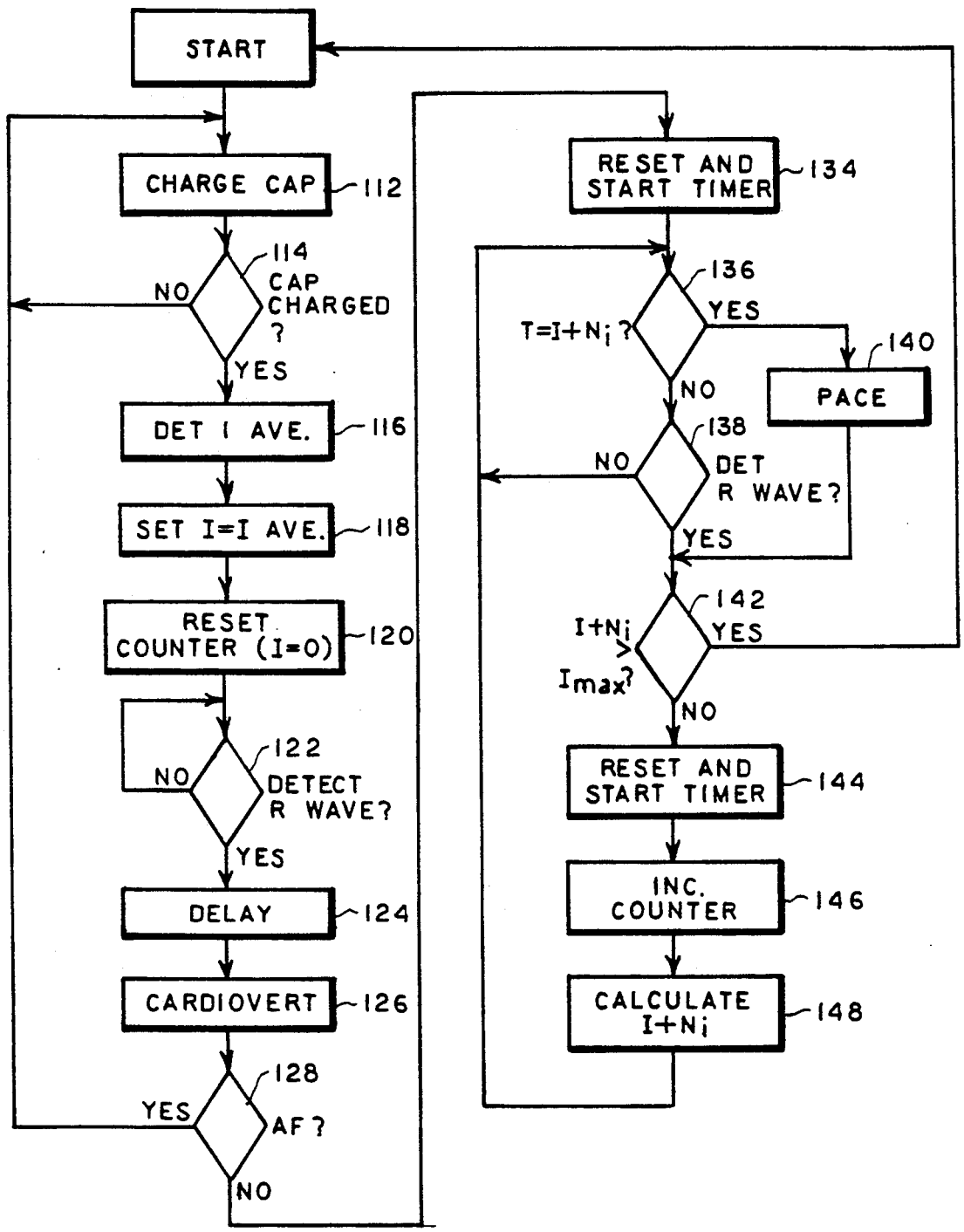
FIG. 2 is a flow diagram illustrating the manner in which the atrial defibrillator of FIG. 1 may be implemented in accordance with the present invention for applying defibrillating or cardioverting electrical energy to the atria of the heart and thereafter gradually returning the cardiac rate of the heart to a preselected normal rate.

Referring now to the flow diagram of FIG. 2, when atrial fibrillation is detected, the microprocessor first, in step 112, causes the charge delivery and control stage 72 to initiate the storage of the cardioverting electrical energy within the storage capacitor of charger and storage capacitor circuit 74. The microprocessor thereafter, at periodic intervals, determines in step 114 if the storage capacitor is fully charged. If it is not, it continues to cause the charge delivery and control stage 72 to charge the storage capacitor. When the storage capacitor is fully charged, the microprocessor then advances to step 116 to determine the base interval upon which the initial pacing rate is to be based. The base interval may be the minimum interval or maximum interval of the last predetermined number of cardiac intervals or a medium interval of the last predetermined number of cardiac intervals. In accordance with this preferred embodiment, the base interval is the average cardiac interval of the heart over a preselected number of cardiac intervals. In performing step 116, the microprocessor utilizes the timer 64, the counter 68, and the average interval stage 66. The timer 64 times the intervals between ventricular activations of the heart detected by the sense amplifier 52 and the R wave detector 54. After a preselected number of cardiac cycles, for example, 10 to 20 cardiac cycles, the average interval stage 66 determines the average interval of the preselected number of cardiac cycles.

The microprocessor then proceeds to step 118 and sets the base interval, which will be utilized to pace the heart after the atria are successfully cardioverted, to correspond to the average cardiac interval determined in step 116. The base interval, by being based upon the average cardiac interval of the last preselected number of cardia cycles, will enable initial pacing of the heart at an initial rate to facilitate the gradual return of the cardiac rate to the final preselected normal rate programmed into the microprocessor 62 from the external control 100.

The microprocessor then proceeds step 120 to reset counter 68. After counter 68 is reset, the microprocessor proceeds to step 122 to determine if a ventricular activation (R wave) is being detected by the sense amplifier 52 and the R wave detector 54. If a ventricular activation is not being detected the microprocessor waits until a ventricular activation is detected. When a ventricular activation is detected, the microprocessor then in step 124 causes the timer 64 to time a delay period of, for example, twenty milliseconds. After the timer 64 times the delay period, the microprocessor 62 in step 126 causes the discharge circuit 76 to discharge the storage capacitor of circuit 74 by a predetermined amount into electrodes 44 and 46 of lead 36. This applies the cardioverting electrical energy to the atria 16 and 18 of the heart for cardioverting the atria. The delayed cardioversion with respect to a detected R wave assures that the cardioverting electrical energy is not applied during an R on T condition as fully described in the aforementioned copending application filed concurrently herewith and which is incorporated herein by reference.

After applying the cardioverting electrical energy to the atria in step 126, the atrial fibrillation detector 70 then, in step 128, determines if the cardioversion was successful in arresting the atrial fibrillation. If it was not, the microprocessor 62 returns to step 112 for performing steps 112 through 126 as previously described.

When the atrial fibrillation detector 70 determines in step 128 that the cardioversion of the atria was successful in arresting the atrial fibrillation, the microprocessor proceeds to step 134. In step 134, the microprocessor resets and starts timer 64.

At this time, the atrial defibrillator 32 has begun the first post-cardioversion pacing interval which is the aforementioned base interval and the timer is timing the base interval. The next three steps, namely steps 136, 138, and 140 implement a demand mode of pacing of the type well known in the pacing art and more specifically, a VVI pacing mode of the ventricles.

In step 136, the microprocessor determines if the timer has completed timing the current interval which, in this case, is the base interval (I) since the count (i) of counter 68 is currently zero and hence $N_i$ is equal to zero. If the timer 64 has not completed timing the base interval (I), the microprocessor then determines in step 138 if a ventricular activation (R wave) is detected. If a ventricular activation is not detected, the microprocessor returns to step 136 to once again interrogate the timer 64. If the timer completes the timing of the base interval before a ventricular activation is detected, the microprocessor will cause the pacer output 78 to pace the ventricles in step 140. However, if a ventricular activation is detected in step 138 before the timer 64 completes the timing of the base interval, the microprocessor will not cause the pacer output 78 to pace the ventricles for the next cardiac interval. As a result, as will be appreciated by those skilled in the art, the foregoing implements VVI or demand pacing.

After step 138 wherein an R wave is detected before the timer 64 completes the timing of the base interval or after step 140 wherein the ventricles are paced, the microprocessor 62, through the interval compare stage 84, immediately compares the last cardiac interval $(I+N_i)$ to the preselected final normal cardiac interval $(I_{max})$ in step 142. If the last cardiac interval is not longer than the final preselected normal cardiac interval, and at this time it will not be since the last cardiac interval is the base interval, the microprocessor 62 immediately in step 144 resets and starts timer 64 and then in step 146 increments counter 68. The count (i) in counter 68 will now be equal to one and the timer is now timing the next cardiac interval which is now $I+N_i$ initiated by either a ventricular activation detected in step 138 before timer 64 completed timing of the base interval or the pacing of the ventricles in step 140.

The microprocessor 62 next, in step 148, through the interval computing stage 82, computes the cardiac interval $(I+N_i)$ currently being timed by timer 64. In performing step 148, and in accordance with this preferred embodiment, the interval computing stage 82 adds an interval time increment $(N_i)$ to the base interval (I). The interval time increments $(N_i)$, for each post-cardioversion pacing interval, may be stored in memory and obtained by the microprocessor in correspondence to the count (i) of counter 68. The interval time increments may, for example, be selected so that each successive cardiac interval represents a decrease in cardiac rate of five beats per second. Alternatively, the interval time increments may be in multiples of a fixed increment so that the first time increment results in a greater decrease in cardiac rate than the later time increment. With either implementation, a gradual return to the preselected normal cardiac rate will result. Once the now current cardiac interval is computed in step 148, the microprocessor returns to step 136 to determine if the ventricles should be paced in accordance with step 140 or not paced in accordance with step 138.

Steps 144, 146, 148, 136, either 138 or 140 and 142 are repeated as necessary until a last cardiac interval is longer than the preselected final normal cardiac interval. When this condition occurs, the cardiac rate will have been gradually decreased from a base rate, such as 150 beats per minute, to a final preselected normal cardiac rate of, for example, about seventy-five beats per, minute in increments of five beats per second per cardiac cycle. Regardless of the manner in which the base rate is determined, whether it be based upon a minimum interval, a maximum interval, a medium interval, or an average interval in accordance with the preferred embodiment herein, the post-cardioversion pacing is implemented at a controlled rate to return the heart to a rate considered normal for a particular patient.

While a particular embodiment of the present invention has been shown and described, modifications may be made, and it is therefore intended to cover in the appended claims all such changes and modifications which fall within the true spirit and scope of the invention.

What is claimed is:

1. An implantable atrial defibrillator for applying cardioverting electrical energy to the atria of a human heart in need of cardioversion and thereafter gradually returning the cardiac rate of the heart to a normal cardiac rate, said atrial defibrillator comprising:
   first detecting means for detecting atrial activity of the heart;
   atrial defibrillation detecting means, responsive to said first detecting means, for determining when the atria of the heart are in need of cardioversion;
   cardioverting means responsive to said atrial fibrillation detecting means for applying the cardioverting electrical energy to the atria of the heart when the atria are in need of cardioversion; and
   pacing means for pacing the ventricles of the heart at a controlled decreasing rate from a base rate to a final rate lower than said base rate after said cardioverting means applies said cardioverting electrical energy to the atria of the heart.

2. An atrial defibrillator as defined in claim 1 wherein said base rate is above seventy-five beats per minute.

3. An atrial defibrillator as defined in claim 1 wherein said pacing means paces the ventricles of the heart at the beginning of consecutive pacing intervals and wherein said atrial defibrillator further includes pacing interval determining means for increasing each said pacing interval after said pacing means paces the ventricles of the heart.

4. An atrial defibrillator as defined in claim 3 further including comparing means for comparing each last said pacing interval to a preselected maximum interval corresponding to said final rate and wherein said pacing means is responsive to said comparing means for terminating the pacing of the ventricles of the heart when a last pacing interval is greater than said preselected maximum interval.

5. An atrial defibrillator as defined in claim 1 wherein said pacing means paces the ventricles of the heart in a demand mode.

6. An atrial defibrillator as defined in claim 5 wherein said demand mode is a VVI mode.

7. An implantable atrial defibrillator for applying cardioverting electrical energy to the atria of a human heart in need of cardioversion and thereafter gradually returning the cardiac rate of the heart to a normal cardiac rate, said atrial defibrillator comprising:
   first detecting means for detecting atrial activity of the heart;
   atrial defibrillation detecting means, responsive to said first detecting means, for determining when the atria of the heart are in need of cardioversion;
   cardioverting means responsive to said atrial fibrillation detecting means for applying the cardioverting electrical energy to the atria of the heart when the atria are in need of cardioversion;
   pacing means for pacing the ventricles of the heart at a controlled decreasing rate from a base rate to a final rate lower than said base rate after said cardioverting means applies said cardioverting electrical energy to the atria of the heart wherein said base rate corresponds to a base cardiac interval; and
   base interval determining means for determining said base cardiac interval in response to said atrial fibrillation detecting means determining that the atria of the heart are in need of cardioversion.

8. An atrial defibrillator as defined in claim 7 wherein said base interval is an average cardiac interval of the heart over a predetermined number of consecutive cardiac cycles.

9. An atrial defibrillator as defined in claim 8 wherein said predetermined number is from ten to twenty.

10. An atrial defibrillator as defined in claim 8 further including second detecting means for detecting ventricular activations of the heart and wherein said base interval determining means is responsive to said second detecting means for averaging the intervals between consecutive detected ventricular activations of the heart over said predetermined number of cardiac cycles of the heart.

11. An atrial defibrillator as defined in claim 7 wherein said base interval is a selected one of a minimum cardiac interval, a maximum cardiac interval, or a medium cardiac interval.

12. A method of applying cardioverting electrical energy to the atria of the human heart in need of cardioversion and thereafter gradually returning the cardiac rate of the heart to a normal cardiac rate, said method comprising the steps of:

detecting atrial activity of the heart;

determining, responsive to detecting the atrial activity of the heart, when the atria of the heart are in need of cardioversion;

applying cardioverting electrical energy to the atria of the heart when the atria of the heart are in need of cardioversion; and thereafter pacing the ventricles of the heart at a controlled decreasing rate from a base rate to a final rate lower than said base rate.

13. A method as defined in claim 12 wherein said base rate is above seventy-five beats per minute.

14. A method as defined in claim 12 wherein said pacing step includes pacing the ventricles of the heart at the beginning of consecutive pacing intervals and increasing each said pacing interval after each said pacing of the ventricles of the heart.

15. A method as defined in claim 14 including the further steps of comparing each last said pacing interval to a preselected maximum interval corresponding to said final rate and terminating the pacing of the ventricles of the heart when a last pacing interval is greater than said preselected maximum interval.

16. A method as defined in claim 12 wherein said pacing step includes pacing the ventricles of the heart in a demand mode.

17. A method as defined in claim 16 wherein said demand mode is a VVI mode.

18. A method of applying cardioverting electrical energy to the atria of the human heart in need of cardioversion and thereafter gradually returning the cardiac rate of the heart to a normal cardiac rate, said method comprising the steps of:

detecting atrial activity of the heart;

determining, responsive to detecting atrial activity of the heart, when the atria of the heart are in need of cardioversion;

applying cardioverting electrical energy to the atria of the heart when the atria of the heart are in need of cardioversion;

pacing the ventricles of the heart at a controlled decreasing rate from a base rate corresponding to a base cardiac interval to a final rate lower than said base rate; and determining said base interval after determining that the atria of the heart are in need of cardioversion.

19. A method as defined in claim 18 wherein said base interval is an average cardiac interval of the heart over a predetermined number of consecutive cardiac cycles.

20. A method as defined in claim 19 wherein said predetermined number is from ten to twenty.

21. A method as defined in claim 19 further including the step of detecting ventricular activations of the heart and wherein said averaging step is performed by averaging the interval between consecutive detected ventricular activations of the heart over said predetermined number of cardiac cycles of the heart.

22. A method as defined in claim 18 wherein said base interval is a selected one of a minimum cardiac interval, a maximum cardiac interval, or a medium cardiac interval.

* * * * *